United States Patent [19]

Ranciato

[11] Patent Number: 4,960,115

[45] Date of Patent: Oct. 2, 1990

[54] BODY SUPPORT APPARATUS

[76] Inventor: Peter Ranciato, 74 School House Rd., Wallingford, Conn. 06492

[21] Appl. No.: 229,003

[22] Filed: Aug. 5, 1988

[51] Int. Cl.$^5$ ............................................. A61F 5/00
[52] U.S. Cl. ........................... 128/87 R; 128/DIG. 20
[58] Field of Search ............ 128/870, 871, 869, 87 R, 128/DIG. 20, 78, DIG. 24; 2/2.1 R, 2.1 A, DIG. 3

[56] References Cited

U.S. PATENT DOCUMENTS

| | | | |
|---|---|---|---|
| 3,521,623 | 7/1970 | Nichols | 128/87 R |
| 3,823,711 | 7/1974 | Hatton | 128/78 |
| 3,823,712 | 7/1974 | Morel | 128/87 R |
| 3,868,952 | 3/1975 | Hatton | 128/78 |
| 3,933,150 | 1/1976 | Kaplan | 128/DIG. 20 |
| 3,982,531 | 9/1976 | Shaffer | 128/DIG. 20 |
| 3,993,056 | 11/1976 | Rabischong | 128/DIG. 20 |
| 4,039,039 | 8/1977 | Gottfried | 128/87 R |
| 4,120,287 | 10/1978 | Rabischong | 128/DIG. 20 |
| 4,169,467 | 10/1979 | Rabischong | 128/DIG. 20 |
| 4,270,527 | 6/1981 | Peters | 128/87 R |
| 4,369,814 | 1/1983 | Humphrey | 2/2.1 R |
| 4,531,516 | 7/1985 | Poole | 128/87 R |
| 4,541,419 | 9/1985 | Osawa | 128/78 |
| 4,624,248 | 11/1986 | Poole | 128/87 R |
| 4,776,327 | 10/1988 | Russell | 128/87 R |

Primary Examiner—Robert A. Hafer
Assistant Examiner—Michael Brown
Attorney, Agent, or Firm—Robert H. Montgomery

[57] ABSTRACT

A support device for enabling paralytics to stand erect, including a flexible housing member having a back portion adapted to be fitted to the back of a paralytic and extending into two leg portions adapted to be fitted to the rear of the legs of a paralytic, an expansible bladder having at least two inflatable chambers is received within the housing, the chambers are joined together at edges thereof to define the back portion and separating into two leg portions, a first strap affixed to the back portion of the housing at the side thereof engaging a paralytiac, one or more other straps are affixed to each of the leg portions of the housing member at the side engaging a paralytic, the first strap is arranged to pass over the chest of a paralytic and secure the back portion to the paralytic, the other strap or straps are arranged to pass around the legs of a paralytic and secure the leg portions to the paralytic. The paralytic may secure the straps himself in a sitting position and then inflate the bladder and the device will lift him to an erect position.

20 Claims, 4 Drawing Sheets

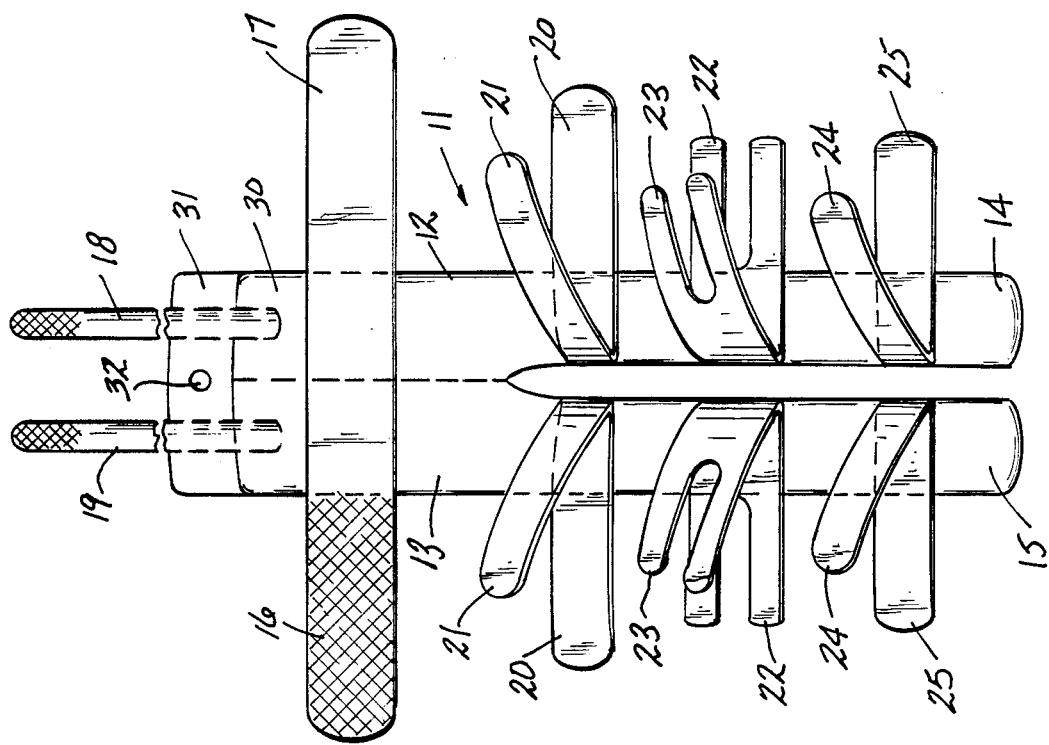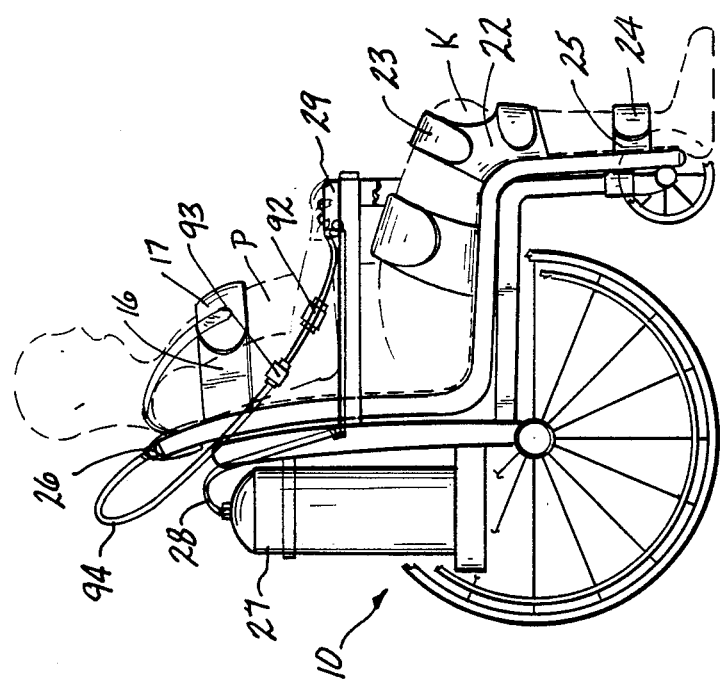

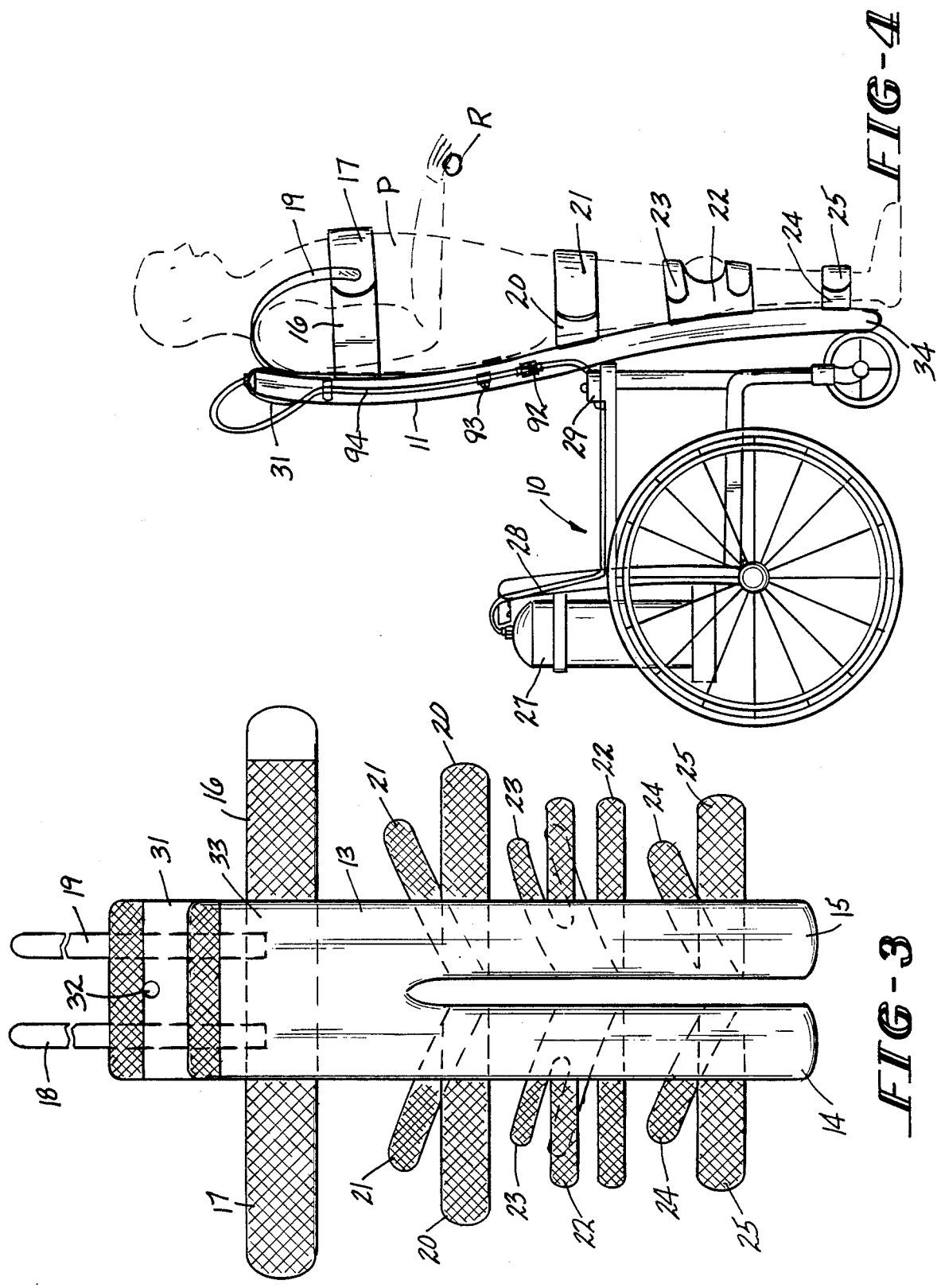

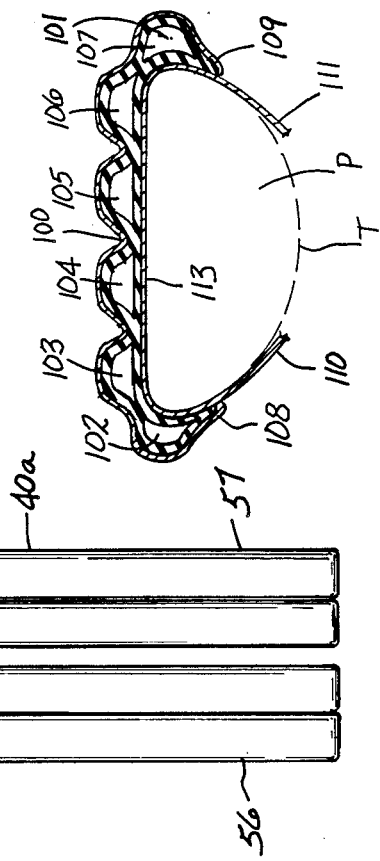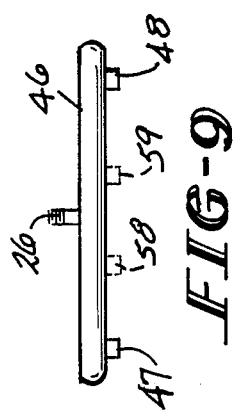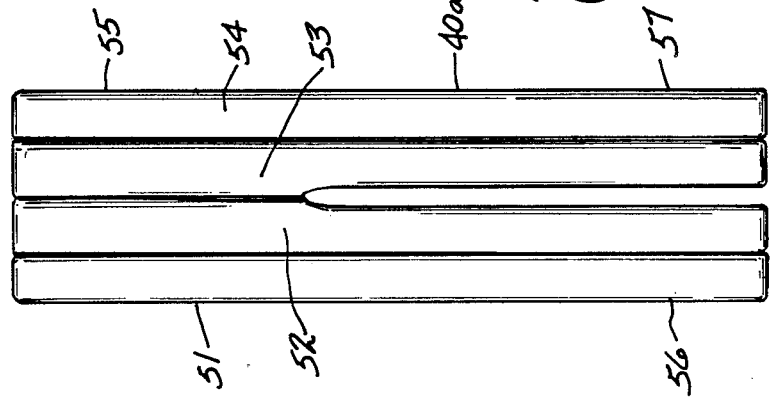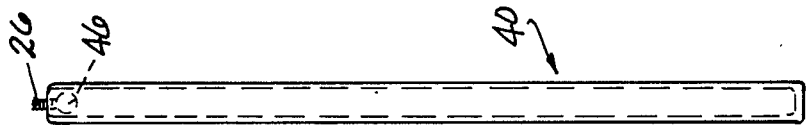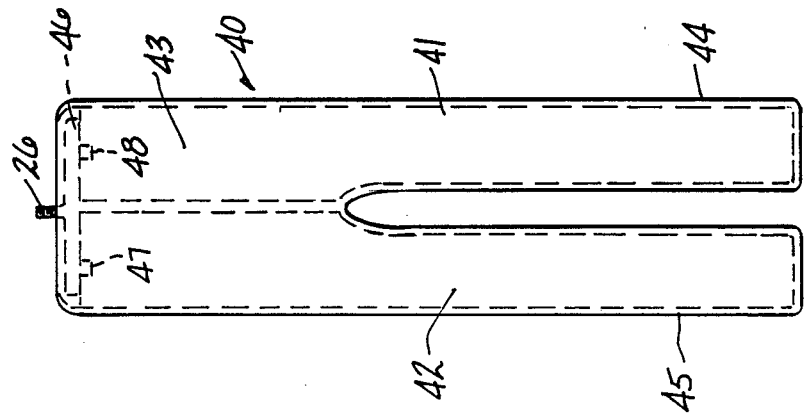

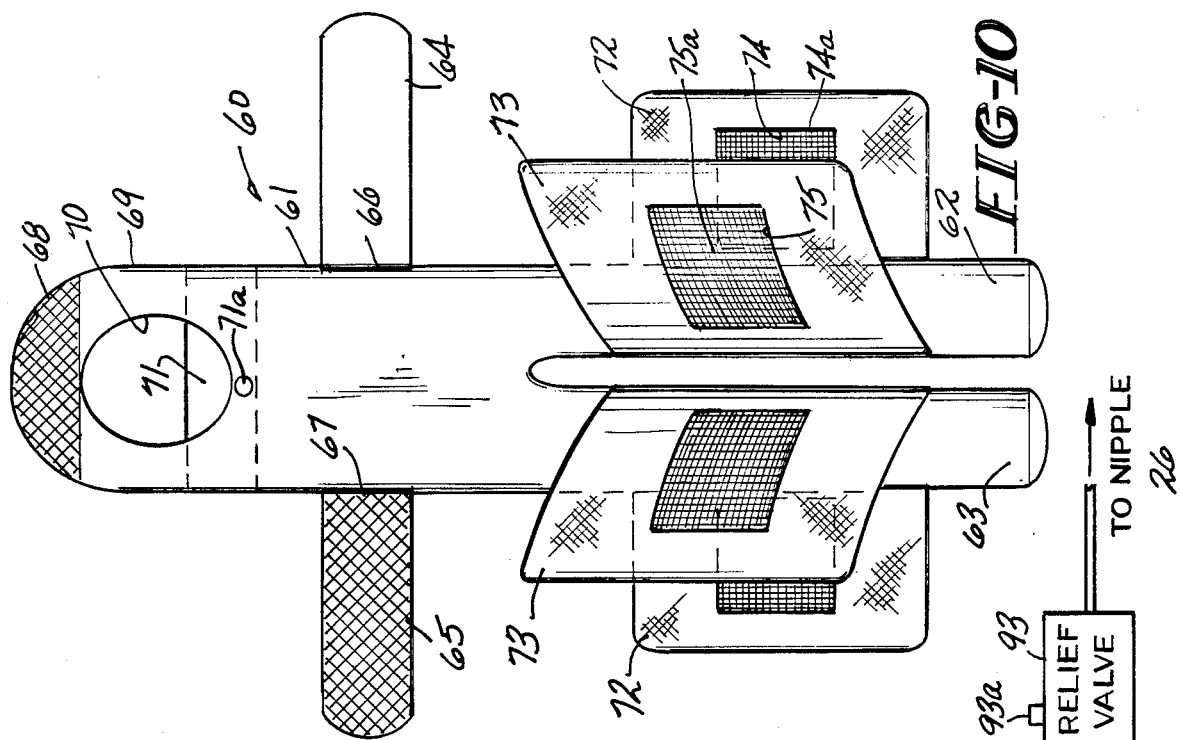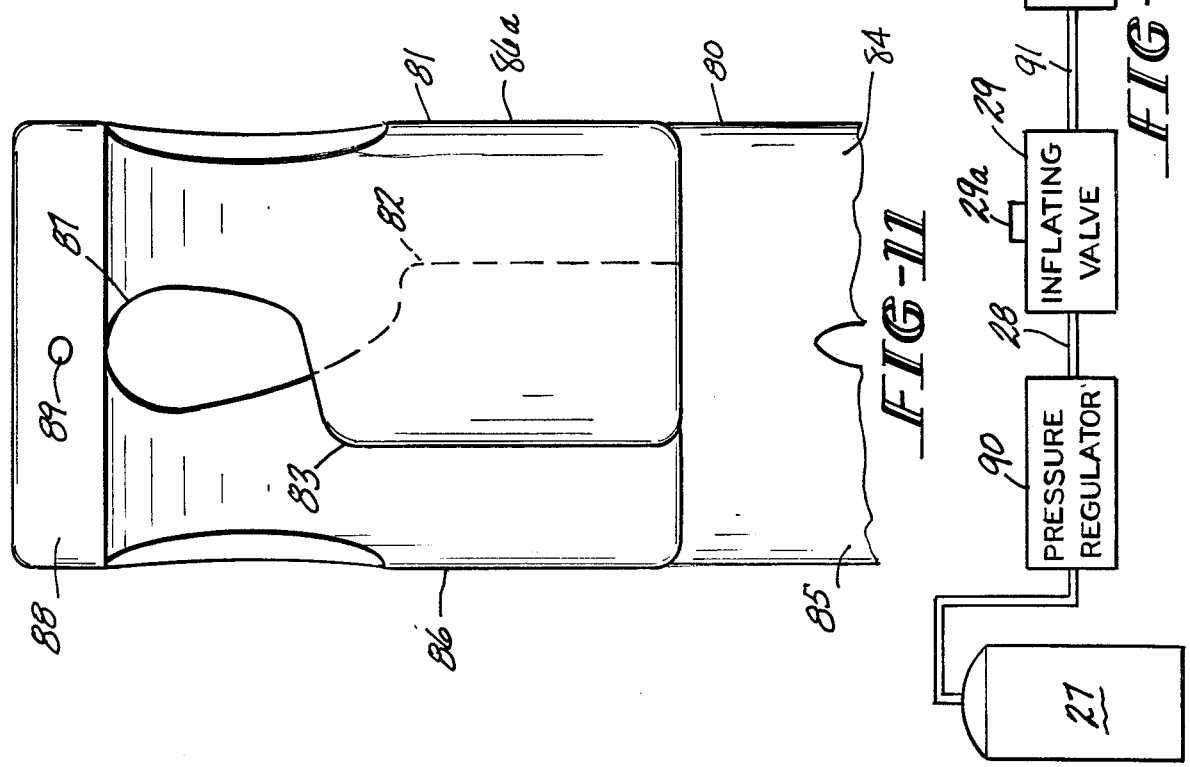

BODY SUPPORT APPARATUS

FIELD OF THE INVENTION

This invention relates to orthopedic appliances for enabling paralytics to stand erect and, more particularly, relates to a pneumatically operated orthopedic appliance.

BACKGROUND OF THE INVENTION

Paralytics, more often referred to as paraplegics, may be paralyzed from the arms down, the location of the initial point of paralysis depending upon the point at which an injury to the spinal column has occurred. Various devices have been devised to enable paralytics to stand and provide support for the legs while in an upright position. However, thus far, none have been known to prove acceptable.

There are metal braces or supports with elastic wrap arounds for the legs which have been strapped to the paralytic. However, these have proven in most cases to be uncomfortable and will tend to bear into or chafe the paralytic.

Pneumatically operated devices have also been proposed, as exemplified in U.S. Pat. No. 3,823,712, which discloses a pair of trousers which have incorporated therein a plurality of separate flexible inflatable longitudinally extending tubes, and it is stated that when the tubes are inflated, they impart to the various portions involved rigidity which will support the paralytic from the waist down.

U.S. Pat. No. 4,169,467 relates to an orthopedic appliance stated to enable paralytics to stand erect and discloses a trouser-like affair which comprises a plurality of separate pieces of clothing to be fitted around body parts located between joints, namely, the hips and knees, and includes inflatable support structure in the form of vertical tubes. This structure further includes mechanical supporting devices joining the separate pieces of clothing.

These devices do not provide spinal rigidity or support for any portion of the torso which may be paralyzed, nor are they suitable to raise a paralytic to an erect position from a sitting position. Neither of these devices is known to have been proven to be successful.

It is desirable for a paraplegic to be in an erect position at times. When in an erect position, the heart pumps better, the kidneys work better, and the entire organic system is enhanced. Additionally, being in an erect position enhances the leg muscles and aids in preventing atrophy of the leg muscles.

Accordingly, the present invention provides a pneumatically operated orthopedic appliance for enabling paralytics to stand erect, which is formed in a single unit and will provide rigid support for the back, commencing at the shoulders and extending to the ankles of the paralytic, and upon inflation, will raise a paralytic from a sitting position to an erect position.

SUMMARY OF THE INVENTION

Briefly stated, the invention in one form thereof comprises a garment or shell member which is three dimensional and is adapted to be fitted to the paralytic about the chest and the legs. This shell is fitted to the back of the paralytic with straps which are fastened to the side of the garment adjacent the back and the back of the legs of the paralytic. The shell has a portion which will be referred to as a back portion, which divides into two leg portions which extend down from the back along the back of the legs of the paralytic.

Received within the housing is a bladder having a plurality of pneumatically independent chambers. These chambers extend from the upper portion of the garment in a back portion and separate into leg portions below the torso.

Means are provided for inflating the chambers with air at a predetermined pressure which may be dependent on the size and weight of the paralytic. The inflation of the chambers does not produce any tightening of the straps due to the point of connection of the straps to the garment or housing.

A device embodying the invention may be placed in a wheel chair which may carry a supply of compressed air, and the paralytic, with or without assistance, may strap himself to the appliance and inflate the chambers which will raise him from the chair to an upright vertical position.

An object of this invention is to provide a new and improved pneumatically actuated orthopedic appliance for enabling a paralytic to stand erect.

Another object of this invention is to provide an orthopedic appliance of the type described which will provide vertical support for the paralytic along the spinal column and rib cage extending essentially the distance of each of the paralytic's legs.

A further object of this invention is to provide a device of the type described which will lift a paralytic from a sitting position to an erect position.

The features of the invention which are believed to be novel are particularly pointed out and distinctly claimed in the concluding portion of the specification. The invention, however, together with further objects and advantages thereof, may best be appreciated by reference to the following detailed description taken in conjunction with the drawings.

BRIEF DESCRIPTION OF THE DRAWINGS

FIG. 1 is a side elevational view of a paralytic sitting in a wheel chair with apparatus embodying the invention affixed to the paralytic;

FIG. 2 is a front view in elevation of apparatus embodying the invention when such apparatus is in a horizontal position and exemplifying the attachment straps;

FIG. 3 is a view similar to FIG. 3, but showing the back of the apparatus;

FIG. 4 is a side elevational view of a paralytic who has been moved upright from a wheel chair when a device embodying the invention has been inflated;

FIG. 5 is an elevation view of a first bladder that is utilized in the invention;

FIG. 6 is a bottom view of the bladder of FIG. 5;

FIG. 7 is a side view of the bladder of FIG. 6;

FIG. 8 is a view similar to FIG. 2, but exemplifying another inflatable bladder which may be utilized in the invention;

FIG. 9 is a detailed view of a manifold which is incorporated in the bladder of FIG. 6 or FIG. 10 to permit inflation of the bladder;

FIG. 10 is a view in elevation of another support apparatus embodying the invention;

FIG. 11 is a view in elevation of still another embodiment of the invention;

FIG. 12 is a schematic diagram of a pneumatic system utilized in conjunction with the invention; and FIG. 13 is a sectional view of another embodiment of the invention.

DETAILED DESCRIPTION OF PREFERRED EMBODIMENTS OF THE INVENTION

FIG. 1 exemplifies a paralytic or patient P seated in a wheel chair 10 with a device 11 embodying the invention which will hereinafter be referred to as a support suit. As shown, the support suit 11 is not inflated. Reference is now made to FIGS. 2-4 in conjunction with FIG. 1. Support suit 11 comprises a flexible shell 12 of a fabric such as nylon, or it may be garment leather, and has what is referred to as a back portion 13 which divides into two leg portions 14 and 15. Shell 12 is hollow and receives therein an inflatable member or bladder as hereinafter described. Straps 16 and 17 are adapted to be secured around the chest of the paralytic P by hook and loop fasteners of the type identified by the trademark "Velcro". The outside of strap 16 also carries one of a hook or loop fastener adapted to secure shoulder straps 18 and 19 having the other of the hook and loop fastener. The shell 12 further has thigh fasteners or straps 20 and 21 for each of leg portions 14 and 15. Also, extending from each leg portion beneath the thigh straps, on each leg, are straps 22 and 23, which are cut out or recessed where they will wrap around a knee K. This facilitates securing of straps 22 and 23 above and below the knee and does not restrict bending of the knee. Additionally, each leg may have calf or ankle straps 24 and 25. All of the mating straps are adapted to fasten to each other by the hook and loop material.

A nipple 26 extends from a bladder within shell 12 and permits the support suit 11 to be inflated from an air pressure source shown as a tank 27 carried on wheel chair 10. As shown in FIG. 1, an air line 28 runs from nipple 26 to a valve 29 on an arm of wheel chair 10. The pneumatic circuitry will be hereinafter explained. When the patient wishes to become erect, he will inflate support suit 11, and as it inflates, it will become rigid and raise the patient P out of wheel chair 10 as shown in FIG. 4.

In FIG. 4, the patient is seen as stabilizing himself by grasping a rod R which may be supported by upright members (not shown). Alternatively, the patient will have crutched by which he will stabilize or balance himself, and also enable him to move. The patient P may also stabilize himself along a horizontal surface or counter, or on parallel bars.

The shell has a front panel 30 as shown in FIG. 2, which includes a flap 31 with an opening 32 therein. Flap 31 on the inside thereof has one of a hook and loop material, and a fold over onto a back panel 33, having the other of the hook and loop material. The nipple 26 extends through opening 32. The front and back panels 30 and 33 are joined by side panels 34 (only one side shown in FIG. 4). These panels define the shell 11. The front and back panels 30 and 33 define an upper opening for receiving an inflatable bladder 40 or 40a as hereinafter described in conjunction with FIGS. 5-9.

Reference is now made to FIGS. 5-7 which show an inflatable bladder 40 which comprises separate longitudinal chambers 41 and 42 which extends longitudinally of the support suit and the patient. The bladder is made of rubber. The two chambers extend from a back portion 43 into leg portions 44 and 45 and receive therein a manifold 46 connected to nipple 26. Manifold 46 has output orifices 47 and 48 extending into each of chambers 41 and 42. The bladder 40 is fitted into shell member 12 which provides restraint for the bladder as it is inflated. The manifold 46 is molded into or otherwise secured to the top of the bladder.

In the alternative, a bladder 40a as shown in FIG. 8 could be formed with longitudinally extending separate chambers 51, 52, 53 and 54, where chambers 52 and 53 are joined at an upper back portion 55, the chambers 51 and 52 extend into a leg portion 56, while the chambers 53 and 54 extend into leg portion 57. In such case, manifold 46 would be provided with additional orifices indicated in broken line in FIG. 9 by the reference numerals 58 and 59 to inflate all four chambers. The back portion and leg portions may be formed from a larger number of a plurality of longitudinally extending chambers. In such case, orifices would be provided on manifold 46 for each of the chambers. Also, the chambers and shell may be so designed and formed to partially wrap around the back and legs of a patient.

In operation, the patient may be sitting in a wheel chair 10, as exemplified in FIG. 1. As bladder 40 is inflated, it will lift the patient from the wheel chair 10 to an upright position, as shown in FIG. 4. Patient P may then be supported in a vertical position at a rail R, counter or may move by the use of crutches, or on parallel bars using his arms.

When the patient wishes to sit again, he may release the air pressure while grasping the arms of the wheel chair and move himself to a sitting position as bladder 40 is deflated, as will hereinafter be described.

FIG. 10 exemplifies another embodiment of the invention which utilizes a shell 60. Shell 60 has a back portion 61 which divides into leg portions 62 and 63. Straps 64 and 65 are affixed at ends 66 and 67 thereof to the edges of shell 60, as by stitching, on the panel of the shell which will be adjacent the patient's back. Strap 65 has one of hook and loop material thereon and strap 64 has the other of the hook and loop material thereon on the back thereof, as viewed in FIG. 10. There will also be one of hook and loop material on the back of strap 65 as viewed in FIG. 10 adapted to cooperate with the other of hook and loop material 68 which is on an extension 69 of back portion 61. Extension 69 has a head opening 70 therethrough. This extension with the head opening replaces the shoulder straps 18 and 19, previously described. A flap 71 similar to flap 31 is also provided to close the opening into shell 60. Flap 71 has an aperture 71a therein to receive nipple 26 therethrough.

Each of the leg portions has a pair of mating straps 72 and 73 which comprises a strap portion 73 connected to the inside of leg 62, and a strap portion 74 connected to the outside of the leg portion 62. The same is true with respect to the straps 72 and 73 on leg portion 63. The straps 72 and 73, in each of portion 74 and 75 thereof, are cut out, and may receive therein a non-hook and loop fabric 74b and 75b. These cutouts are designed to be across the knee of the patient and allow the knee to freely bend. The length in the height direction of the straps 72 and 73 is such that the knee will reside in the areas of the cutouts 74 and 75. The paralytic may then affix the straps 72 and 73 together to both his thighs and calves with facility. The straps 64 and 65 will fit about the chest of the patient in a manner similar to that discussed in conjunction with FIGS. 2-4. This construction requires a lesser effort on the person to affix the support apparatus to himself.

Reference is now made to FIG. 11 which shows still another embodiment of the invention utilizing a shell 80 having a vest type construction 81 with overlapping panels 82 and 83 having mating hook and loop materials thereon to provide support about the chest. Here, the leg portions 84 and 85 are broken, partially cut away, since the leg straps are as previously described in conjunction with FIG. 10. The vest panels are stitched to the front edges of the front panel of shell 80 along edges 86 and 86a thereof and further stitched at 87 to the top front edge of shell 80. A closure flap 88 having an opening 89 for receiving a nipple 26 is also stitched to the front panel of shell 80.

The shell and all embodiments shown may be made with either a garment grade leather or, in the interest of reducing weight, it may be constructed of a synthetic material such as nylon. Prototypes have been made with both materials. In the case of the nylon shell, a 400 denier Nylon fabric was used. Additionally, for cushioning purposes, the nylon shell was made with composite panels of nylon, two layers of nylon sandwiching a thin layer of foamed material, such as polyurethane.

FIG. 12 schematically defines a pneumatic system used in conjunction with the invention. The tank 27 contains air under pressure which is supplied to a pressure regulator 90 (not shown in FIGS. 1 and 4). The pressure regulator may be mounted to the tank 27. An air line 28 leads from the pressure regulator to inflating valve 29. The patient P may operate valve 29. The line 91 leads from inflating valve 29 to a quick disconnect coupling 92 and hence to a pressure relief valve 93. To inflate the support suit, the patient will actuate valve 29 through a button 29a, slide or other control device. The inflating valve 29 is of the type which has a pressure limiting feature which will shut off when the pressure in line 91 reaches a predetermined value. At this point, the paralytic P will be upright, as shown in FIG. 4. At this time, the paralytic P may open the quick disconnect 92 to free himself from line 91. The quick disconnect 92 includes a check valve which will prevent any escape of air from the bladder. When the paralytic P wishes to reseat himself, he will stand with his back to the wheel chair 10 and actuate a pressure relief valve 93 in line 94 and bleed the air from the bladder. Pressure relief valve 93 also has an actuating device 93a to bleed air from the bladder. The line 94 is then hanging free or it may be attached to a clip or a pocket in a side panel 34 of shell 11.

In the alternative, the pneumatic systems would be arranged to bleed the air from the bladder through valve 29 after the quick disconnect had been reconnected.

The invention has been disclosed as comprising a bladder received within a hollow restraining shell, which presently is considered a preferred embodiment of the invention. However, the retaining fastening straps may be directly attached to the bladder and the shell eliminated. Alternatively, in apparatus embodying the invention, the outer fabric may be bonded to the bladder to provide restraint upon inflation.

FIG. 13 exemplifies another embodiment of the invention showing a shell 100 which is bonded to a bladder 101 defining six individual chambers 102, 103, 104, 105, 106, and 107, about the torso T of a patient P. The outer chambers 102 and 107 extend partially about the back of the torso T. The shell and bladder have extreme flanges 108 and 109 to which are attached straps 110 and 111, respectively, which may be attached about the chest of a patient P in the same manner as straps 16 and 17 or 64 and 65, as previously described, or vest panels 82 and 83, as described in conjunction with FIG. 11.

The bladder 101 is enclosed on the side of the back of patient P by a covering 113 of a fabric construction previously described.

In the case of a support suit as shown in FIG. 13, the chambers 104 and 105 are split below the torso into leg portions as previously explained. Each of the chambers 102-107 inflates individually from the shoulder or above of the patient, and is defined individually so as not to cause a large bulge on the back of the patient. Again, as previously described, the strap or vest panels 110 and 111 are attached to panels or extensions adjacent the back of the patient, so that upon inflation, expansion of the bladder is outward of the patient and will not cause compression of the chambers against the patient.

In some instances, it may be desirable to restrain the ankles of a patient P as the bladder is inflated and raises the patient P from a sitting position. This may be accomplished by pivotal rods vertically extending from the wheel chair having a low L-shaped arm. The rods will initially be positioned to restrain the ankles of the patient and then turned away to permit the patient to move from the wheel chair.

It may thus be seen that the objects of the invention set forth, as well as those made apparent from the foregoing description, are efficiently attained. While preferred embodiments of the invention have been set forth for purposes of disclosure, modifications to the disclosed embodiments of the invention, as well as other embodiments thereof, may occur to those skilled in the art. Accordingly, the appended claims are intended to cover all embodiments of the invention and modifications to the disclosed embodiments which do not depart from the spirit and scope of the invention.

Having thus described the invention, what is claimed is:

1. A support device for enabling paralytics to stand erect, comprising an inflatable flexible, housing member having a back portion adapted to be longitudinally fitted to the back of a paralytic and extending into two leg portions adapted to be fitted to the rear of the legs of a paralytic, said housing member defining inflatable chambers, said chambers being joined together at edges thereof at said back portion and separating into leg portions, a first securing means affixed to said back portion of said housing at the side thereof for engaging a paralytic, other securing means affixed to each of the leg portions of said housing member at the side thereof for engaging a paralytic, said first securing means arranged to pass over the chest of a paralytic and secure said back portion to the paralytic, said other securing means being arranged to pass around the legs of a paralytic and secure said leg portions to the paralytic, said housing member upon inflation of said chambers being effective to raise a paralytic to an erect position.

2. The device of claim 1 further including means controllable by the paralytic for inflating said housing member.

3. The device of claim 2 further including means controllable by the paralytic for deflating said housing member.

4. The device of claim 1 where said housing member defines an even plurality of inflatable chambers, and said chambers separate into two leg portions, each having an equal number of said chambers.

5. The device of claim 4 where all of said chambers are longitudinally continuous from said back portion to the extremities of said leg portions.

6. The device of claim 5 where said back portion wraps partially around the sides of the torso of the paralytic.

7. The device of claim 5 where said leg portions wrap partially around the legs of the paralytic.

8. The device of claim 1 where said chambers are defined in a member of resilient material, and a restraining member is bonded to said resilient material.

9. The device of claim 1 further including a manifold in said housing for directing air under pressure to each of said chambers.

10. The device of claim 1 where said second securing means comprises straps positioned to surround the thighs and calves of the paralytic while leaving the knees free to bend.

11. The device of claim 1 where said first securing means comprise vest-like flaps arranged to be secured around the torso of a paralytic.

12. The device of claim 1 further including means arranged to fit over the shoulders of a paralytic and attach to said first securing means.

13. A support device for enabling paralytics to stand erect, comprising a flexible housing member having a back portion adapted to be longitudinally fitted to the back of a paralytic and extending two leg portions adapted to be fitted to the rear of the legs of a paralytic, an expansible bladder having at least two inflatable chambers received within said housing, said chambers being joined together at edges thereof and separating in said leg portions, a first strap affixed to said back portion of said housing at the side thereof engaging a paralytic, other straps affixed to each of the leg portions of said housing member at the side engaging a paralytic, said first strap arranged to pass over the chest of a paralytic and secure said back portion to the paralytic, said other straps being arranged to pass around the legs of a paralytic and secure said leg portions to the paralytic.

14. The device of claim 13 further including means controllable by the paralytic for inflating said bladder.

15. The device of claim 14 further including means controllable by the paralytic for deflating said bladder.

16. The device of claim 13 where said bladder comprises an even plurality of inflatable chambers, and said chambers separate into two leg portions, each having an equal number of said chambers.

17. The device of claim 16 where all of said chambers are longitudinally continuous from said back portion to the extremities of said leg portions.

18. The device of claim 13 where said second securing means comprises straps positioned to surround the thighs and calves of the paralytic while leaving the knees free to bend.

19. The device of claim 13 where said first securing means comprise vest-like flaps arranged to be secured around the torso of a paralytic.

20. The device of claim 13 further including means arranged to fit over the shoulders of a paralytic and attach to said first support means.

* * * * *